(12) United States Patent
McGill et al.

(10) Patent No.: US 8,132,443 B2
(45) Date of Patent: Mar. 13, 2012

(54) MICROFABRICATED GAS CHROMATOGRAPH

(75) Inventors: R Andrew McGill, Lorton, VA (US); Rekha Pai, Alexandria, VA (US); David R. Mott, Burke, VA (US); Jennifer L Stepnowski, Alexandria, VA (US); Viet Nguyen, Gaithersburg, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 294 days.

(21) Appl. No.: 12/434,180

(22) Filed: May 1, 2009

(65) Prior Publication Data
US 2009/0272270 A1 Nov. 5, 2009

Related U.S. Application Data

(60) Provisional application No. 61/071,489, filed on May 1, 2008.

(51) Int. Cl.
*B01D 53/02* (2006.01)
(52) U.S. Cl. .................. 73/23.39; 73/23.42; 96/101
(58) Field of Classification Search .............. 96/101; 73/23.35, 23.39, 23.42
See application file for complete search history.

(56) References Cited

U.S. PATENT DOCUMENTS

| | | | | |
|---|---|---|---|---|
| 3,149,941 A * | 9/1964 | Barnitz et al. | ............ | 96/101 |
| 3,538,744 A * | 11/1970 | Karasek | ............ | 73/23.39 |
| 4,935,040 A | 6/1990 | Goedert | | |
| 5,641,400 A * | 6/1997 | Kaltenbach et al. | ....... | 210/198.2 |
| 5,792,943 A * | 8/1998 | Craig | ............ | 73/61.52 |
| 5,888,390 A * | 3/1999 | Craig | ............ | 210/198.2 |
| 5,997,708 A * | 12/1999 | Craig | ............ | 204/601 |
| 6,015,869 A | 1/2000 | Grate et al. | | |
| 6,068,684 A | 5/2000 | Overton | | |
| 6,068,780 A * | 5/2000 | Yu | ............ | 216/10 |
| 6,454,840 B1 * | 9/2002 | Gellert et al. | ............ | 96/101 |
| 6,489,774 B1 * | 12/2002 | van de Goor et al. | ......... | 324/439 |
| 6,607,580 B1 * | 8/2003 | Hastings et al. | ............ | 95/87 |
| 6,663,697 B1 | 12/2003 | Kottenstette et al. | | |
| 6,666,907 B1 | 12/2003 | Manginell et al. | | |

(Continued)

OTHER PUBLICATIONS

Pai et al., "Microfabricated Gas Chromatograph for Trace Analysis," 2008 IEEE Conference on Technologies for Homeland Security, May 12-13, 2008.

(Continued)

*Primary Examiner* — Robert Clemente
(74) *Attorney, Agent, or Firm* — Amy L. Ressing; Rebecca L. Forman (57) ABSTRACT

The present invention is generally directed to a microfabricated gas chromatograph column having two patterned substrates, each optionally having a stationary phase material coating, bonded together to provide a continuous flow channel. The flow channel can have a serpentine arrangement or a modified serpentine arrangement comprising alternating series of consecutive turns in one direction where each series has enough turns to move carrier gas and analyte molecules from the center of the column cross section to an outer wall of the channel or from one outer wall of the channel to the opposite outer wall. Different portions of the substrates can be coated with differing thicknesses of stationary phase material and/or with different stationary phase materials. The column can have a circular cross-section or a semi-circular cross-section where the flat portion of the cross-section has grooves. Also disclosed is the related method of making the microfabricated gas chromatograph column.

23 Claims, 9 Drawing Sheets

U.S. PATENT DOCUMENTS

| | | | |
|---|---|---|---|
| 6,670,024 B1 * | 12/2003 | Yu | 428/209 |
| 6,701,774 B2 | 3/2004 | Srinivasan et al. | |
| 6,759,013 B2 * | 7/2004 | Kaltenbach et al. | 422/504 |
| 6,838,640 B2 | 1/2005 | Wise et al. | |
| 6,911,611 B2 | 6/2005 | Wong et al. | |
| 7,060,521 B2 * | 6/2006 | Leonardsson | 438/52 |
| 7,078,548 B2 * | 7/2006 | Houser et al. | 556/431 |
| 7,273,517 B1 | 9/2007 | Lewis et al. | |
| 7,744,818 B2 * | 6/2010 | Iwamoto et al. | 422/88 |
| 2005/0139536 A1 | 6/2005 | Belov et al. | |
| 2006/0144237 A1 * | 7/2006 | Liang et al. | 96/101 |
| 2006/0231494 A1 | 10/2006 | Lu et al. | |
| 2009/0178563 A1 * | 7/2009 | Masel et al. | 96/101 |

OTHER PUBLICATIONS

Pai et al., "Design and Simulation of a Microfabricated Gas Chromatographic Column," Proceedings of the ASME 2008 International Design Engineering Technical Conferences and Computers and Information in Engineering Conference, New York, NY, Aug. 3-6, 2008.

Mott et al., "Analysis and Design of Novel Column Geometries for Micro-Gas Chromatography," 47th AIAA Aerospace Sciences Meeting, Orlando, FL, Jan. 5-8, 2009.

* cited by examiner

FIG. 8 a) 180 left - 360 right - 180 left b) 360 left - 720 right - 360 left

MICROFABRICATED GAS CHROMATOGRAPH

PRIORITY CLAIM

This Application claims priority from U.S. Provisional Application No. 61/071,489 filed on May 1, 2008 by R. Andrew McGill et al., entitled "MICROFABRICATED GAS CHROMATOGRAPH FOR TRACE ANALYSIS OF ILLICIT SUBSTANCES," the entire contents of which are incorporated herein by reference.

BACKGROUND OF THE INVENTION

1. Field of the Invention

The present invention relates generally to gas analyzers and, more specifically, to microfabricated gas chromatography for trace analysis.

2. Description of the Prior Art

Ever since its inception, the standard in volatile mixture separations for analysis has been gas chromatography (GC). Traditional GC involves injecting the analyte mixture into a tubular column which is coated with a stationary phase or packed with a relatively inert porous material that is itself coated with a stationary phase. A common configuration is a wall coated fused silica capillary column. Depending on the carrier gas flow conditions in the column, the analyte boiling points and relative affinities for and interaction with the stationary phase, the different components of the analyte mixture elute from the column at various times (retention times). As the chemicals elute or exit the end of the column, they are detected and identified by a detector with the result displayed as a chart known as a chromatograph—response (y-axis) versus retention time (x-axis). In short, the chromatograph provides a spectrum of peaks representing the separated analytes present in an injected mixture eluting from the column at different times. Both retention times and the order of peaks will be constant for similar conditions and will yield a quick identification of the components. The process can be tuned for improved resolution and speed with temperature and pressure programming.

Quantitative analysis can also be carried out as the area under a peak is proportional to the amount of analyte present. By integrating and thus calculating the area under the peak, the concentration of an analyte in the original sample can be determined. In general, substances that vaporize below 300° C. (and therefore are stable up to that temperature) can be measured quantitatively.

Figure 1:
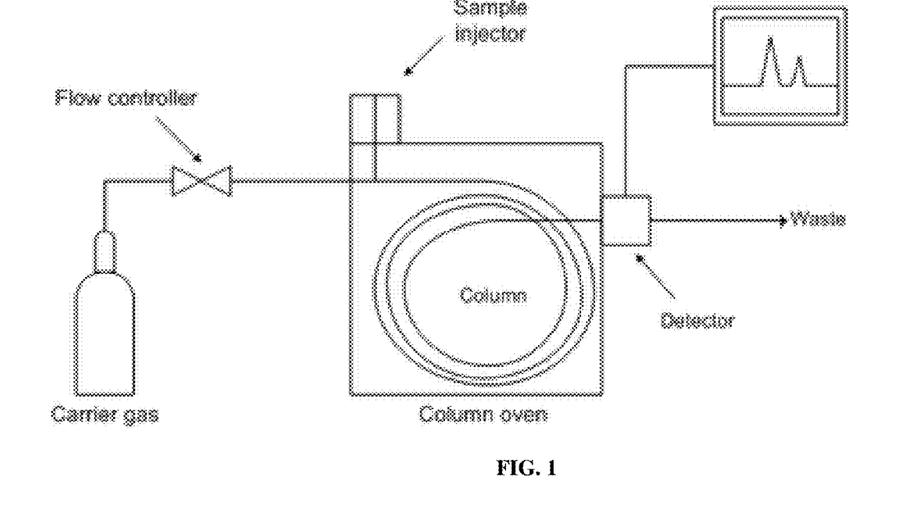
FIG. 1 shows a depiction of a typical gas chromatograph.

Typical gas chromatographs consist of an injector system, a carrier gas supply, a capillary column coated with a polymeric stationary phase, a detector, and the associated control electronics for sampling, heating, and acquisition of data (FIG. 1). Conventional GC systems are expensive bench top instruments that require high power and offer typical analysis times measured in tens of minutes. Recently, microfabrication techniques have been applied to analytical systems to develop miniaturized systems that could allow analytical systems to be fabricated with sizes comparable to a wrist watch. Micromachining allows batch-fabricated devices with high quality control and the potential for inexpensive portable systems that consume minimal power. Furthermore, the thermal mass of microfabricated devices is small and direct heating allows rapid thermal ramping with much faster rates than in typical gas chromatographs, allowing a reduction in analysis times. These attributes make these devices attractive for a number of applications involving on-site monitoring of environmental samples.

When an analyte is injected into a GC column, it is normally vaporized just prior to entering the column. Depending on the injection method, fluidic design, flow conditions, and vaporization efficiency, a vapor band of analyte enters the column with some finite time width. In an ideal column, the band would retain its original time width throughout the length of the column. However, undesirable band broadening processes are prevalent in all commercial columns leading to a loss in chromatography separation power. Some features that lead to band broadening processes include non-uniform stationary phase coatings (eddy diffusion), diffusion limited analyte processes (resistance to mass transfer between mobile and stationary phases), and longitudinal diffusion processes that derive from high concentration areas (center of band) moving into low concentration areas (edge of band). In conventional capillary columns, polymer stationary phase coatings are coated by filling the column with a solution of polymer, capping one end, and pulling at a reduced pressure on the other end to slowly remove solvent from the column leaving behind a polymer coating. In newer microfabricated columns, the inside surfaces of the column may not be smooth and wherever there are sharp discontinuities such as a corner, stationary phase polymer material can undesirably pool during the deposition process or during subsequent movements that can occur at elevated temperatures.

BRIEF SUMMARY OF THE INVENTION

The aforementioned problems are overcome in the present invention which provides a microfabricated gas chromatograph column having two patterned substrates, each optionally having a stationary phase material coating, bonded together to provide a continuous flow channel. The flow channel may have a serpentine arrangement or a modified serpentine arrangement comprising alternating series of consecutive turns in one direction where each series has enough turns to move carrier gas and analyte molecules from the center of the column cross section to an outer wall of the channel or from one outer wall of the channel to the opposite outer wall. Different portions of the substrates can be coated with differing thicknesses of stationary phase material and/or with different stationary phase materials. The column can have a circular cross-section or a semi-circular cross-section where the flat portion of the cross-section has grooves. Also disclosed is the related method of making the microfabricated gas chromatograph column.

The present invention has many advantages over the prior art to mitigate band broadening and tailing problems and to ensure all molecules of a single type experience about the same number of molecular interactions with the stationary phase for the same length of time. Allowing coating deposition before permanently joining two halves of the column enables the use of a variety of coating techniques that are not possible with conventional column coating techniques. Moreover, different segments (along the column) or halves (e.g., upper/lower) of a single column may be coated with different stationary phases without having to coat separate columns and join them together with the risk of adding additional "dead volume". Different thicknesses of the polymer stationary phase may be coated along the column length for a gradated thickness. In particular, the thickness of the stationary phase may be particularly thick at the column entrance or be composed of a different sorbent material or mixture of sorbent materials. This can act to trap and focus analytes of interest prior to local heating of the column inlet to release them into the column length without any associated "dead volume" mixing problems associated with other injection techniques. Areas of the column that include geometrical discontinuity can be selectively excluded from the coating procedure. Additionally, designing one surface of the column with recessed grooves fosters local or advective mixing at these points and overcomes diffusion limited processes to promote transport across the column (i.e. perpendicular to the carrier gas flow) which accelerates the process to reach analyte distribution equilibrium between the carrier gas and the stationary phase. This reduces band broadening and tailing.

These and other features and advantages of the invention, as well as the invention itself, will become better understood by reference to the following detailed description, appended claims, and accompanying drawings.

BRIEF DESCRIPTION OF THE DRAWINGS

FIG. 6(a) shows oxide/nitride or plain Si wafer. FIG. 6(b) shows back side metallization for heaters. FIG. 6(c) shows bis-benzocyclobutene (BCB) spun onto the wafer. FIG. 6(d) shows photoresist applied. FIG. 6(e) shows dry etch patterning. FIG. 6(f) shows wet/dry etching of the column. FIG. 6(g) shows sorbent coating of the column. FIG. 6(h) shows alignment and bonding.

FIG. 7(a) shows that the stationary coating is of uniform thickness (t). Performance and pressure drop are limited by the radius. FIG. 7(b) shows that the stationary coating thickness is non-uniform. The polymer coating thickness has values ranging from t on the sides to T at the corners. Also, there is a dead phase at the corners. Performance or interaction (diffusion) is limited by the width. Pressure drop is controlled by the height of the column.

FIG. 8(a) is a flow schematic. FIG. 8(b) shows the result of one 90° turn. FIG. 8(c) shows the result of two 90° turns. FIG. 8(d) shows the result of four 90° turns. FIG. 8(e) shows the result of six 90° turns. FIG. 8(f) shows the result of eight 90° turns. FIG. 8(g) shows the result of twelve 90° turns. FIG. 8(h) shows the result of sixteen 90° turns.

FIG. 9(a) shows a bend geometry of 180° left-360° right-180° left. FIG. 9(b) shows a bend geometry of 360° left-720° right-360° left.

FIG. 12(a) shows features pointing upstream. FIG. 12(b) shows features pointing downstream.

DETAILED DESCRIPTION OF THE INVENTION

The present invention generally relates to microfabricated portable gas analyzers with high sensitivity and selectivity that may be used in applications such as chemical and biological agent detection, explosives detection, toxic industrial chemical detection, environmental monitoring, food and water screening, and medical diagnostics and treatment. A component of these analyzers is the gas chromatograph column which is used for separations of an injected mixture based on the relative sorption of the various analytes in the carrier gas by the stationary phase. One embodiment of the present invention is the design of the gas chromatograph column. A serpentine layout (and a modified serpentine layout) design with a circular cross-section has been simulated using computational fluid dynamic (CFD) modeling to help optimize chromatography performance. The column design comprises two halves: one half has a semi-circular cross-section while the other half can have a semi-circular cross-section or be flat with micron-sized grooves cut into it to encourage inertial mixing irrespective of the flow rate. A further embodiment of the present invention is the fabrication of the column. Low temperature adhesive bonding of two patterned substrates is used to join together pieces of a micro gas chromatograph. This allows coating of the stationary phase before permanently bonding the upper and lower pieces of the gas chromatography column and the ability to check the integrity and quality of the coating prior to permanent bonding. This also allows a wide range of coating techniques to be used to deposit the stationary phase. The stationary phase can be deposited only where desired, thus avoiding depositing the stationary phase in areas where polymer pooling could be prevalent. The substrates may comprise any suitable material (e.g., silicon, glass, quartz, silicon nitride, silicon on insulator (SOI), or any combination thereof). An even further embodiment of the invention is the coating used as the stationary phase. Sorbent coatings, such as a hydrogen bond acid (HBA) sorbent polymer (e.g., HCSFA2 [see U.S. Pat. Nos. 7,153,582 and 7,078,548]), can provide selectivity to hydrogen bond basic (HBB) analytes (e.g. TNT, DMMP, GB, VX) and have been demonstrated to provide $10^6$ higher partition coefficients than commercially available stationary phases like polydimethylsiloxane (PDMS). HCSFA2 is a hyperbranched carbosilane polymer with functional hexafluoroisopropanol (HFIP) groups with a high affinity to reversibly bind HBB analytes such as phosphonate ester nerve agents and explosives. The collection efficiency of HCSFA2 or its efficacy does not change over millions of thermal cycles even during high temperature (>250° C.) operating conditions in air. This is particularly attractive for GC-on-chip applications in which air can be used as the carrier gas consequently eliminating the need for specialized gas cylinders for sources of inert carrier gas.

Production wise, the low temperature (<250° C.) bonding methodology and the isotropic profile allows for uniform stationary phase coating and gradation in coating thicknesses or no coating at places such as turns to improve resolution. This is not possible in traditional or microfabricated GC columns using static coating methods on physically whole columns where the stationary phase in solution is used to fill the column and the solvent is slowly removed by sealing one end and applying a reduced pressure at the other so that the solvent evaporates leaving a thin coating on the interior walls. In addition, the present invention allows for the coating of any number of different sorbent coatings at various points in the single column and in a fashion that they are not overlapping and without any additional dead volume that is normally associated with joining different sorbent coated columns. The more conventional coating approach, where the stationary phase in solution is used to fill the column and the solvent is slowly removed by sealing one end and applying a reduced pressure at the other so that the solvent evaporates leaving a thin coating on the interior walls, can be applied when the 2 column pieces are temporarily joined. Subsequent to coating, these pieces can be separated and joined to other column pieces coated likewise but with another stationary phase, or joined to a planar column piece that may contain the groove structures to facilitate advective mixing to overcome diffusion limited processes in the carrier gas phase.

The methods of making the microstructure devices described herein are described below. These methods are fully discussed to enable the invention, but the intended scope of the invention includes any methods of manufacture, including those discovered in the future, that produce the devices claimed and described herein.

Design and Fabrication
Column Layout

Figure 2:
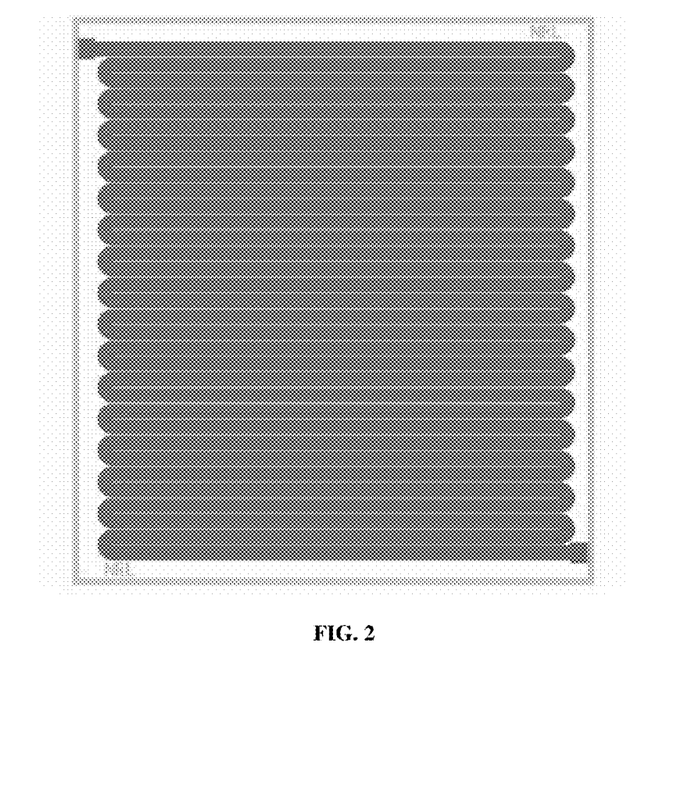
FIG. 2 shows a serpentine layout of a micro gas chromatograph die.

For the present invention, the column has a circular cross-section geometry laid out in a serpentine fashion on the die (FIG. 2). In experiments, a circular cross-section with a 250 μm internal diameter was used to allow larger practical flow rates while retaining suitable chromatography performance. Other attempts at fabricating a micro gas chromatograph so far have concentrated on a rectangular cross-section laid out in a spiral design on a die. While the microfabricated spiral design mimics the conventional capillary column, which is a flexible fused silica capillary with a polyimide cladding wound into a coil with a low radius of curvature, in efforts to maximize the area on the die, the micro version's inner turns have a high radius of curvature. Theoretically, these tight turns moving towards the center usually lead to a race-track effect and band broadening or artifacts in the analyte peaks. The serpentine layout allows similar lengths as the spiral design to be laid out on comparable die areas. Additionally, with the serpentine layout there are no major changes (in terms of radius of curvature) that the analyte band encounters during its journey from the inlet to the outlet. Moreover, CFD simulations predict that the sharp turns in this serpentine column configuration help in analyte mixing (perpendicular to carrier gas flow), which can increase the interaction with the stationary phase coating significantly and hence enhance resolution.

The microfabricated gas chromatograph is made up of two half circles aligned and sealed together using an adhesive bond to mimic a traditional capillary conduit. Another possible design utilizes the same half-circle cross-section but with grooves cut on a flat base to promote mixing perpendicular to carrier gas flow to improve chromatography performance.

Fabrication Process

The methodology used to bond the micro gas chromatograph pieces of the present invention involves the low temperature (<250° C.) bonding of two patterned wafers using an intermediate layer of adhesive. Any suitable adhesive may be used that can be applied below a temperature that would decompose the stationary phase material. Some examples include bis-benzocyclobutene, cytop, and norland. The adhesive used in experiments was bis-benzocyclobutene sold under the brand name Cyclotene® by Dow Chemical Company. The thickness of the bonding adhesive should be kept to a minimum and preferably result in a polymeric layer with a high glass transition point or crystalline properties to reduce the possibility of any significant analyte interactions to any exposed surface of the adhesive. A non polar property of any exposed surface of the adhesive is preferred. The joining of two halves under relatively low temperature conditions enables novel coating techniques to be used prior to bonding and improved quality control when compared with existing methods. Existing microfabricated gas chromatographs typically include anodic bonding of the patterned silicon column with a rectangular cross-section with a Pyrex® glass top. The temperature required for this sort of process is >450° C. and the application of a high electric voltage. These conditions are not compatible with typical stationary phases used in chromatographic applications. Therefore, in these designs, and as is normally the case, the column is coated with the stationary phase after the column is permanently bonded. This can result in non-uniform deposition of the stationary phase, especially in areas of discontinuity or sharp corners. In addition, when a column is coated after bonding, it is very difficult to characterize and determine the quality of the sorbent coated column without employing some destructive means.

Figure 3:
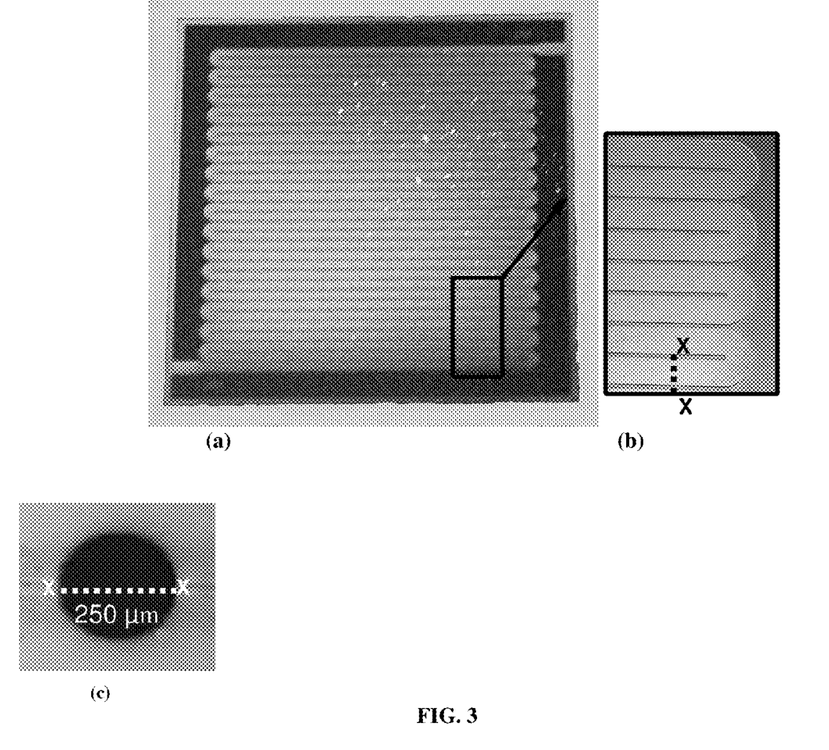
FIG. 3 shows optical microscope images of a micro gas chromatograph (a) complete die, (b) expanded view of the die, and (c) cross-section at bond interface.
Figure 4:
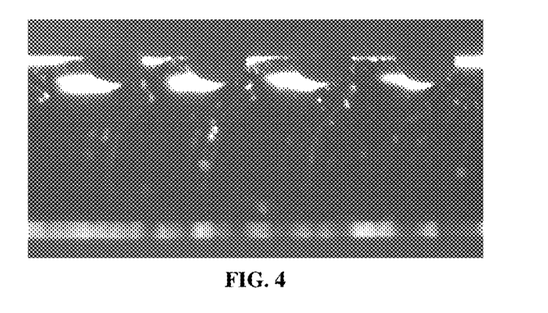
FIG. 4 shows an isotropic profile (250 μm diameter) obtained with a $XeF_2$ etch for a micro gas chromatograph.
Figure 5:
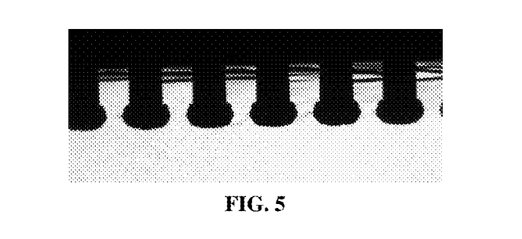
FIG. 5 shows an etch profile obtained with a Bosch process on the DRIE that could be modified by polishing to obtain an isotropic profile for the micro gas chromatograph.

As shown in FIG. 3, the two halves of the column can be created by isotropically etching silicon using a wet etch typically a mixture of hydrochloric acid, nitric acid and acetic acid mixture (HNA) or a dry vapor etch process with xenon difluoride ($XeF_2$). The masking materials used for this silicon etch may be silicon nitride, thermal oxide, the adhesive (e.g. bis-benzocyclobutene), photoresist or any combination thereof. Elevated temperatures of about 50-60° C. and stirring can be used during the HNA etch to promote etchant diffusion thus accelerating the etch rate and the isotropic profile. A simple photolithography step with positive resists S1813 (MicroChem Corp) or AZ P4330 (MicroChemicals GmbH) followed by a dry etch in a reactive ion etching (RIE) system (mixture of $CF_4$ and $O_2$) can be used to pattern these hard masks. Alternatively, the isotropic etch can also be accomplished by a $XeF_2$ dry etch (FIG. 4) or a variation of the $SF_6/CF_4$ Bosch etch on the deep reactive ion etching system similar to FIG. 5 (although the Bosch etch may require an additional step of chemical mechanical polishing to get rid of the necking effect seen in FIG. 5).

Figure 6:
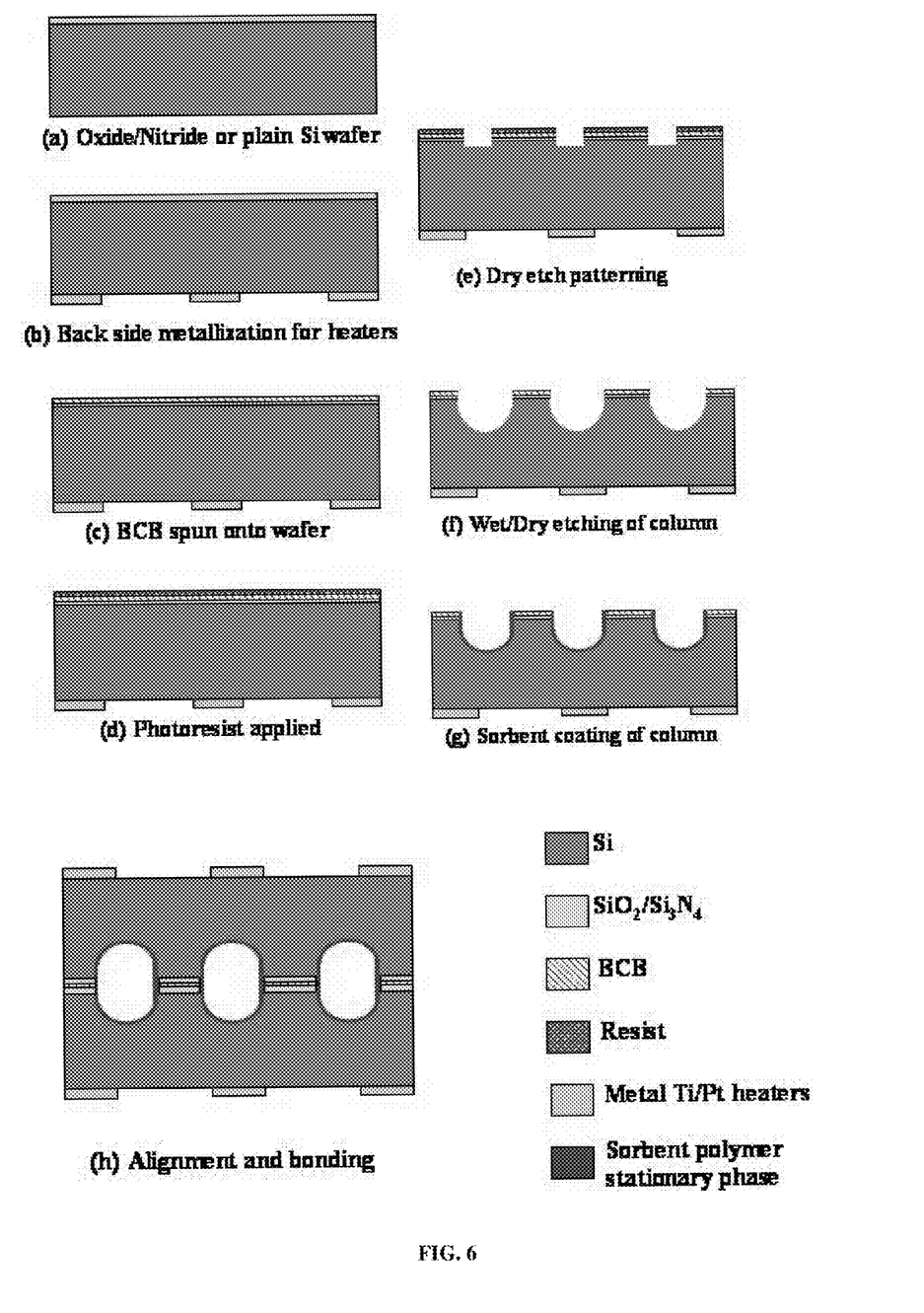
FIG. 6 shows a general process flow for the fabrication of a micro gas chromatograph (not drawn to scale).

The two halves can be coated with a stationary phase and later bonded using a patterned adhesive bis-benzocyclobutene yielding a circular column. The bonding process can be carried out in an oven at 150-250° C. for a few hours while maintaining a constant flow of nitrogen or argon through the oven. FIG. 6 shows a detailed illustration depicting the complete fabrication process flow. It is important to avoid leaks. A mismatch in the top and bottom halves may provide a leaky path through which carrier gas and analyte may escape into the atmosphere with a resulting loss in signal response. To ensure a good seal, alignment of the features on the top and bottom halves can be achieved by inserting pieces of commercially available capillary columns into the microfabricated inlet and outlet. The inlet and outlet can be positioned on opposite sides of the die and in plane with each other to provide easier alignment. Additionally, a variation in this design is to etch the inlet and outlet ports out of plane from the column itself enabling an easier alignment and integration with commercial capillaries as well as stacking of multiple chips. Also, there may be an inlet and outlet design that flares out to the outer diameter of the 250 μm inner diameter commercial capillary to ensure a tight seal by using short straight pieces of conventional capillary column (deactivated) to more easily interface to injector and detector assemblies. Additionally, the alignment of the two halves can be achieved with an accuracy of ±1 μm by utilizing a backside aligner such as the AB-M or Karl Suss system. Besides the flared out connections, additional alignment may by provided by "dovetail joints"—a series of pins made in one half interlock with a series of tails micromachined into the other half of the micro GC. The pins and tails may have any sort of shape such as trapezoidal, circular or square—but they are complementary, i.e., one is a protrusion while the other is its negative and hence an etched out feature. They can be fabricated at the same time as the capillary columns with no additional steps or masks needed. These alignment features may be placed either at the four corners of the die or in between the patterns for additional alignment accuracy. These may also be coated with the adhesive to ensure a good bond. Windows made by thinning the silicon or silicon nitride in the substrate enabling IR alignment may also be used. Uncured photoresist may also be used to form a tacky bond during and after alignment of the two patterned halves. Other methods to make the micro GC include the use of glass on one half photolithographically patterned with Norland optical adhesive which is UV-curable on a mask aligner achieving alignment and bonding in the same step.

Column Variations

CFD simulations show that varying either the column diameter (constrictions or widening) or the depth can lead to more mixing and resolution by introducing lateral flow that exchanges fluid near the walls with fluid in the core of the column. Microfabrication allows for this variation in geometry and depth, which cannot be accomplished in the fused silica capillaries used in traditional gas chromatography.

Additionally, a re-oxidation process may be used—the corners of the column can be rounded off by oxidizing the patterned columns in a furnace under a constant flow of oxygen at 1100° C. As this process can be tailored to growing nanometers of oxide by varying temperatures and times, this could be carried out to ensure that there are no sharp or pointed extremities and to provide a more perfect half-circle for the gas chromatograph before stationary phase coating or final bonding.

Reduction in Thermal Mass

One advantage of the on chip gas chromatographic design is the reduction in power requirements for any required thermal control. The reduction in footprint size to a planar configuration not only confers portability but also requires significantly less power to control the column temperature. Power requirements in the milliwatts of power range are possible because heat can be efficiently applied directly to the column. The thermal oxide or nitride used as a masking layer in the present invention was selected so that in a further iteration, the columns can be suspended by etching back to these layers. This step further reduces the thermal mass of the micro gas chromatographs and also eliminate hot spots in the column. To analyze low vapor pressure analytes such as chemical warfare agents and explosives, temperature programming can be readily applied to micromachined designs.

Coating Technology

Figure 7:
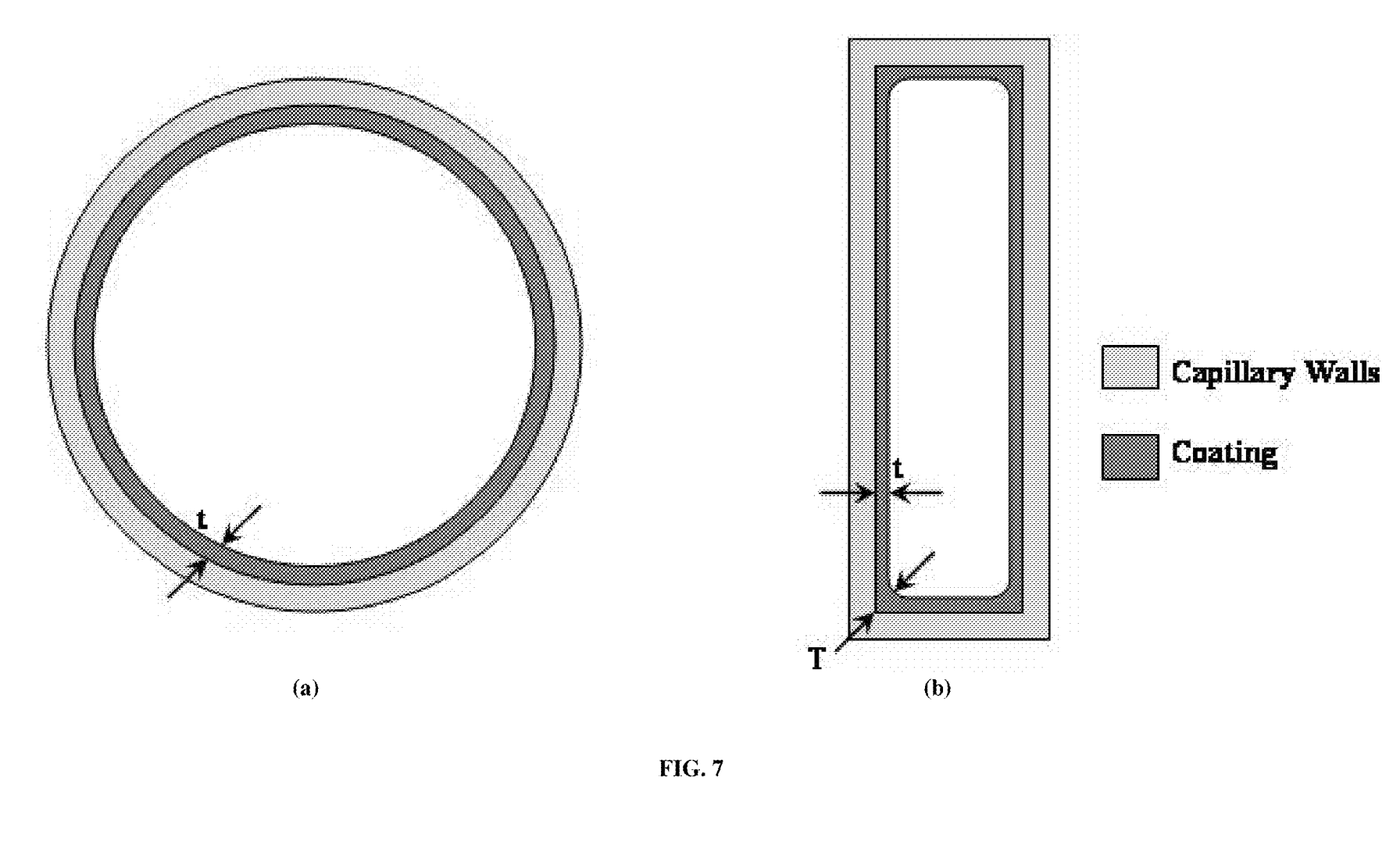
FIG. 7 shows a comparison of stationary phase coatings for columns with (a) a circular cross-section and (b) a rectangular cross-section.

Existing microfabricated columns are typically fabricated with a rectangular cross-section mainly due to the ease in construction. Although these columns have lower pressure drops, their performance is compromised by the presence of sharp corners that can result in non-uniform stationary phase coatings which leads to a degradation in chromatography performance through a loss in resolution (band-broadening in peaks). However, the microfabricated gas chromatograph of the present invention contains a circular cross-section which allows the stationary phase coating to be more easily maintained as a uniform film. In addition, the present invention allows the stationary phase to be selectively deposited if desired to avoid coating in areas of geometrical column discontinuity. This yields improved chromatographic resolution when compared to a rectangular or square cross-section keeping all other parameters such as coating thickness, column length, gas flow, etc., constant. An illustration showing the effect of the cross-section on coatings is depicted in FIG. 7.

Easier Characterization of the Column

Static coating procedures are the most common method used for applying the sorbent stationary phase to the inner wall of the capillary gas chromatographic column. This technique involves two basic steps. First, it requires filling the column with a solution of the sorbent stationary phase dissolved or suspended in a solvent. One end of the column is capped, and the solvent is then removed by applying a reduced pressure at the other end while warming the column to a suitable temperature. The pressure and temperature are optimized for the type of sorbent being applied. This method has several drawbacks. The coating thickness as well as any variability in the film cannot be directly determined without cutting and, thus, damaging the column. This technique also does not allow for unique stationary phase applications such as coating different controlled thicknesses in various parts of the column, special sorbents with varying functionalities in a segmented fashion along the column or leaving a portion of the column uncoated.

The micro-fabricated column of the present invention can be coated prior to permanently joining its two halves. This ability to coat prior to sealing will allow for characterization of the coating thickness and morphology which helps identify areas of poor coating and uneven thickness.

Coating Methods

The present invention allows a number of deposition techniques to be employed. For example, one or both of the two halves can be coated using ink jet printing techniques. One half or both halves of the column can be coated lying flat or the column half or halves could be coated at an angle which will work with gravity to distribute the sorbent stationary phase within the column as desired. In addition, the column being coated can be moved in a rotary fashion with respect to the deposition nozzle to achieve a more even distribution across the curvature of the groove. Once coated with the stationary phase, the two column halves can be clamped together and heated while spinning to more evenly distribute the stationary phase. An aluminum or stainless steel casing with C clamps or screws may be used to retain the alignment and to ensure there is no shift during the spinning and bonding process. The halves can then be disassembled and interrogated to determine coating thickness and morphology. These coating application variations are not possible with current GC technology. The ability to coat the two halves flat may also facilitate addition of the stationary phase application to an overall microfabrication process reducing the cost of production.

Varying Thicknesses (Including No Sorbent) and Different Sorbent Materials in the Same Column In the present invention, sorbent material can be applied to only the portions of the column where most mixing occurs. Other portions of the column may be left uncoated (e.g., turns of a serpentine column), resulting in similar resolution but faster chromatography. Furthermore, different portions of the column may be deliberately prepared with different thicknesses of stationary phase. For example, sorbent coatings can be applied thickly at the inlet to concentrate analytes at the inlet of the column creating a simple but effective focusing zone/injector within the same column. These concentrated vapors can be subsequently released by heating locally the thicker coated inlet into the much more thinly coated portion of the column. Current technology requires the column to be joined to the injector which can be a source of leaks, dead volume, band broadening effects, and additional cost. A gradated coating thickness with a thicker coating at the injector end of the column may also allow the column to operate with a larger sample size range, so that the initial injected sample does not overload the stationary phase at the column inlet.

For improved separation of mixtures as well as selectivity, different parts of the column can be coated with any number of stationary phases with unique functionalities in a segmented fashion or the two halves of the column can be coated with different stationary phases. Currently, two different capillary columns must be separately coated and joined in order to create a two dimensional gas chromatograph (separation is effected with two gas chromatographic columns with different stationary phases such as polar and non-polar). With the present invention, a single column can be coated with one coating for a portion of the column and then another portion of the column can be coated with a different sorbent. This would eliminate the junction currently needed which can be a source of leaks, "dead" volume, and additional length to the column.

The sorbent can be applied to only one half of the two column halves as well. This way, the uncoated half of the column can be passivated and designed with grooves to promote transport across the column (i.e. perpendicular to the carrier gas flow) which accelerates the process to reach analyte distribution equilibrium between the carrier gas and the stationary phase, while the coated half provides the stationary phase for separation, thus improving resolution of analytes.

Cross-Linking of Coating to the Column Substrate

In the present invention, the substrate material, e.g. silicon, can be chemically modified to allow polymer grafting and crosslinking of the stationary phase to the wall of the column. Cross-linking the stationary phase increases longevity of the column and reduces column bleed which lowers the signal baseline and improves sensitivity to analytes of interest. Possible column substrate materials include among others silicon, glass, and quartz.

CNTs as Coatings

By making the two semi-circular halves of the gas chromatograph separately out of silicon before sealing makes it possible to incorporate various materials as stationary phases. One such candidate would be carbon nanotubes (CNTs), including single-walled and multi-walled CNTs. CNTs, due to their large surface-to-volume ratios, act as "sorbent rods" to organic molecules. Also, their conductance changes according to gas compositions, and functional groups could be added on for improved specificity, thus conferring an additional layer of selectivity towards organophosphates or other analytes of specific interest. These CNTs could be integrated into the miniaturized gas chromatograph in at least two different ways: (1) the substrate used, e.g. silicon, can withstand the normal high temperature process for CNTs (>600° C.) allowing for an in-situ growth; and (2) dispersions of CNTs can be spray-coated, spun-on, or ink-jetted down and the solvent can be evaporated to get an even thickness of stationary phase before bonding the two halves. An embodiment of the CNTs as a stationary coating is a conformal mat on the walls of the gas chromatograph. This scheme will increase the surface sites for sorbing without a significant change in pressure drop as compared to an uncoated gas chromatograph with the same dimensions. Furthermore, the high surface area of the CNTs can be utilized to maximum advantage in sorbing toxic chemicals by fabricating a dense mesh out of them that fills the entire volume of the gas chromatograph. The CNTs could be grown straight up from the floor and walls of the gas chromatograph thus maximizing the interaction of the analyte with the stationary phase.

Computational Fluid Dynamic Simulation for the Design and Development of the Micro Gas Chromatograph Mass transport is critical to the success of traditional gas chromatography systems, but diffusion processes also introduce limitations to the performance and operation of these systems. Diffusive transport across the capillary (i.e., perpendicular to the primary carrier gas flow direction) carries molecules from the high-speed core flow region to the capillary wall, homogenizing the average velocity of these molecules in the mobile phase and facilitating the interaction of these molecules with the stationary phase to achieve the separation. If the flow rate of the mobile phase is too high, diffusion may not occur quickly enough to homogenize the residence time of the molecules of a given species or effectively facilitate interaction with the walls. If the flow rate is too low, diffusion along the primary carrier gas flow direction will spread the peak for each constituent in the separation, again undermining performance.

By modifying the geometric design of the traditional capillary column used in micro gas chromatography, the reliance on diffusion to generate cross-channel transport can be greatly reduced or eliminated. Repeated bends in the column direction or geometric features within the column can be used to promote fluid transfer between the core of the flow stream that, in contrast to diffusion, is either independent of flow rate or amplified at higher flow rates. For the micro gas chromatograph of the present invention, extensive computational fluid dynamic (CFD) modeling has been utilized to characterize fluidic flow in various column designs.

Curved Channel Geometries

Curved-column channel geometries are used in micro gas chromatography applications to make the column more compact and to minimize the footprint of the device. Differences between column layouts, such as comparing serpentine channels to spiral channels, have previously been documented. Some limited modifications to the channel cross-section have also been cited as affecting system performance, but such modifications have been limited to minor changes to a traditional serpentine design near the channel bends. There are currently no devices that exploit sequences of engineered bends tailored to maximize the impact of the modified flow field on system performance.

Secondary flow generated in curved geometries is characterized by the Dean number (Dn) defined for a curved circular tube in Equation (1).

$$Dn = \frac{2\rho u r}{\mu}\sqrt{(r/R)} = Re\sqrt{(r/R)} \quad (1)$$

In Equation (1), $\rho$ is the fluid density, u is the mean velocity, r is the tube radius, $\mu$ is the dynamic viscosity, and R is the radius of curvature of the centerline of the tube. The grouping in front of the radical is the Reynolds number (Re) based on tube diameter, which is a similarity parameter indicating the importance of inertial effects relative to viscous effects. The Dean number indicates the importance of centripetal acceleration based on the inertia (as measured by the Reynolds number) and the turn radius, with higher values of Dn indicating a stronger secondary flow generated due to the curvature. Howell et al. (Howell et al., "Design and Evaluation of a Dean Vortex Based Micromixer," Lab on a Chip, Vol. 4, No. 6, pp. 663-669 (2004), the entire contents of which are incorporated herein by reference) demonstrated that flow in curved channels with square cross-sections generate secondary flow for Dn as low as 3.36.

Figure 8:
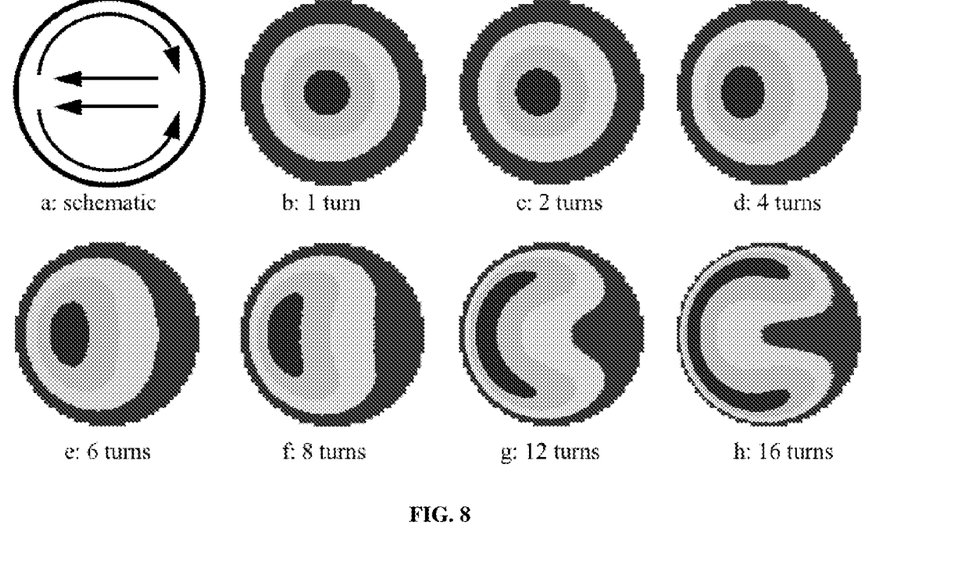
FIG. 8 shows the effect of repeated 90° turns on the fluid distribution in the cross-section of a circular tube.

For a prototype micro gas chromatograph system of one embodiment of the present invention, the carrier gas was air, r=125 µm, and R=150 µm. Under the expected operating conditions of 1 mL/min and 100° C., Re=3.7 and Dn=3.4. FIG. 8 demonstrates the effect of repeated 90° turns in the fluid distribution with the tube under these flow conditions. The shading of the fluid in the cross-section indicates the initial distance from the channel centerline, and the left side of each cross-section is the outside wall in the turn. The flow schematic in FIG. 8a demonstrates the secondary flow that is generated by the turn: a vortex pair pushes core fluid toward the outer wall to the left. After several consecutive turns, the fluid initially at the core of the tube (darkest shading) has migrated into a long thin line close to the tube wall.

Figure 9:
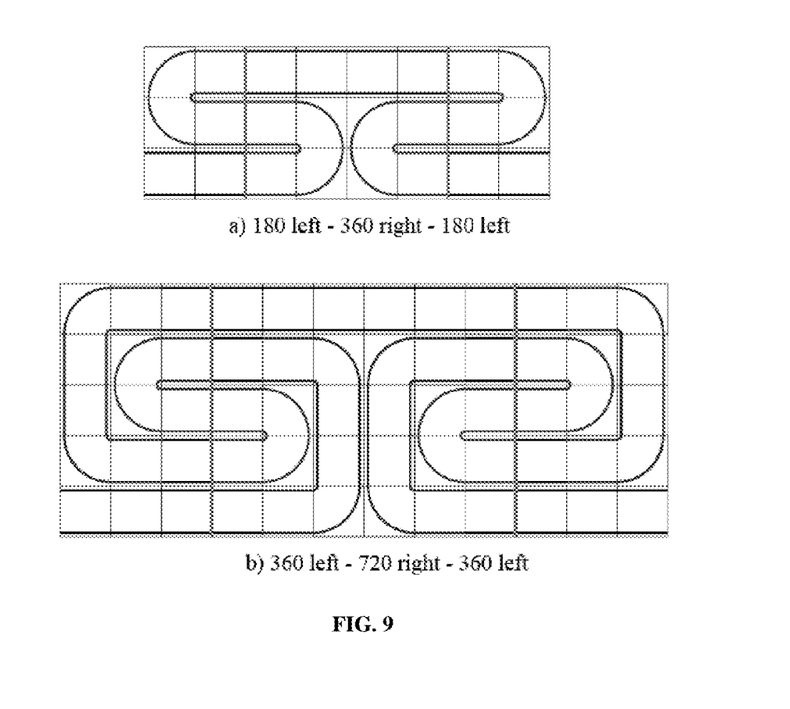
FIG. 9 shows column designs that exploit repeated bend geometries to facilitate fluid exchange between the core and near-wall regions.

FIG. 9 demonstrates how to construct a column geometry employing several consecutive turns with the same orientation to redistribute fluid within the column. The number of turns and the sizing of straight sections connecting the turns can be optimized for particular low rates and values of the diffusion coefficient. In this manner, the design can be tuned to overcome diffusion limitations in transporting fluid from the core to close to the wall while leaving the fluid close to the wall long enough for the species present to interact sufficiently with the stationary phase.

Internal Geometric Features

Figure 10:
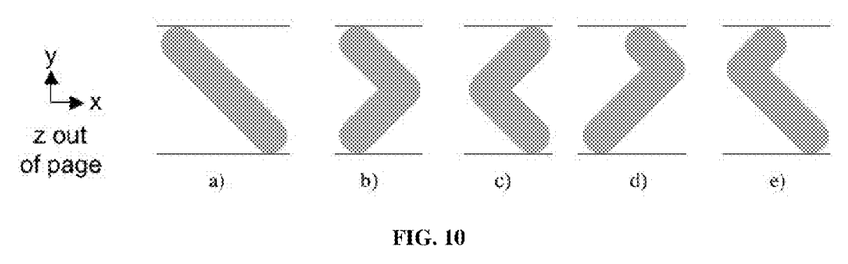
FIG. 10 shows typical groove shapes that can be added to a conduit to generate secondary flow.
Figure 12:
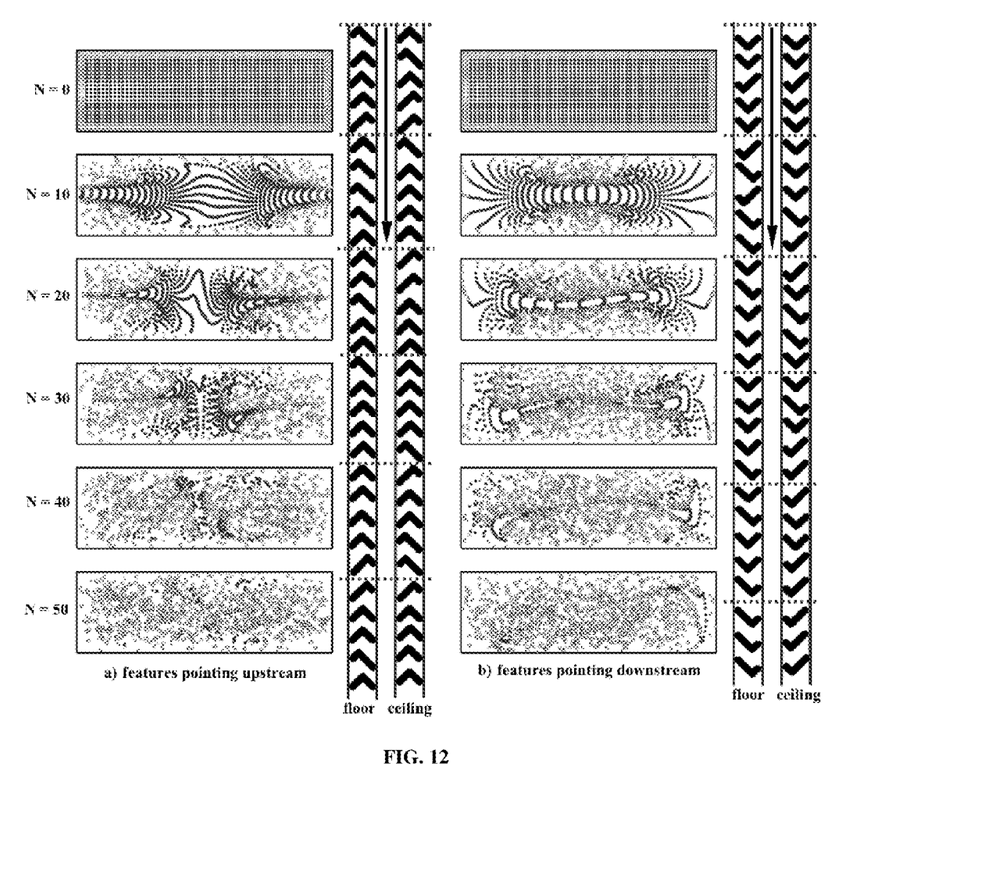
FIG. 12 shows designs for enhancing surface delivery in a rectangular microchannel. Open symbols indicate particles that have met the prescribed threshold for close approach to a channel wall, and filled symbols indicate particles that have not.
Figure 13:
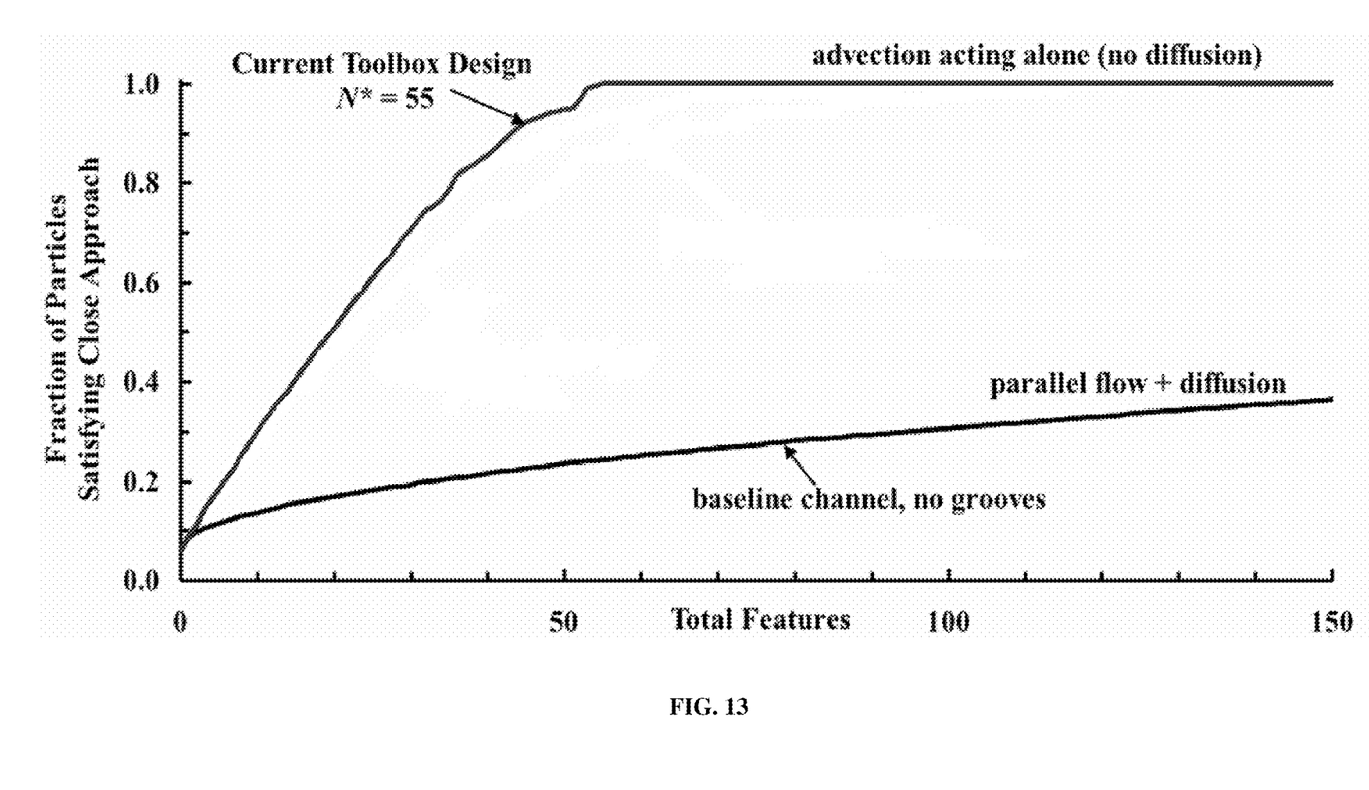
FIG. 13 shows CFD simulation results comparing the number of analyte molecules that reach the walls with and without grooves providing advective mixing in a rectangular microchannel. The lower line is for a baseline channel with no grooves (parallel flow plus diffusion). The upper line is for a channel with grooves using Current Toolbox Design N*=55 (advection acting alone—no diffusion).

Adding static geometric features to a fluid conduit, such as grooves cut into the floor or ceiling of a microchannel, can also generate a cross-channel flow and facilitate fluid redistribution to enhance the performance of a chromatography system. Toolbox software for the rapid analysis, design, and optimization of components of this type has been applied to design optimal mixers and components that enhance surface delivery for explosives detection applications (Mott et al., "Toolbox for the Design of Optimized Microfluidic Components," Lab on a Chip, Vol. 6, No. 4, pp. 540-549 (2006); Mott et al., "Designing Microfluidic Components for Enhanced Surface Delivery Using a Genetic Algorithm Search," AIAA-2008-688, 46th AIAA Aerospace Sciences Meeting and Exhibit, Reno, Nev., Jan. 7-10, 2008, Mott et al., "Analysis and Design of Novel Column Geometries for Micro-Gas Chromatography," AIAA-2009-1122, 47th AIAA Aerospace Sciences Meeting and Exhibit, Orlando, Fla., Jan. 5-8, 2009, the entire contents of each are incorporated herein by reference). This software takes a user-specified performance metric as input and uses a genetic algorithm search to determine the optimal sequence of features to perform the specified task. FIG. 10 illustrates typical groove shapes that are included in the feature library, and FIG. 12 provides examples of feature combinations that enhance surface delivery in rectangular channels that were found automatically given a surface delivery metric (Mott et al., "Designing Microfluidic Components for Enhanced Surface Delivery Using a Genetic Algorithm Search," AIAA-2008-688, 46th AIAA Aerospace Sciences Meeting and Exhibit, Reno, Nev., Jan. 7-10, 2008). For these two design calculations, a set of particles (molecules) was released into the channel, and the genetic algorithm was asked to find the sequence of groove shapes that forced all of these particles close to the wall in as short a distance downstream as possible. Close was defined as 10% of the channel height. The design on the left could choose only the two shapes in FIGS. 10c and 10e, and the design on the right could choose from only those shapes in FIGS. 10b and 10d. These designs in FIGS. 12a and 12b drive every particle tracked in the simulation below the prescribed threshold for close approach in 59 and 55 features, respectively. The best mixer design previously available in the literature required 136 features to accomplish this same task.

Figure 11:
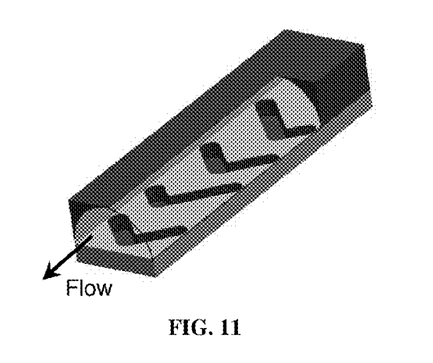
FIG. 11 shows a perspective drawing of a micro gas chromatograph with typical groove shapes etched on the floor for advective mixing.

Applied to micro gas chromatography, designs can be developed that consist of a semi-circular cross-section with grooves cut into the flat floor of the conduit as shown in FIG. 11. Metrics that combine surface delivery and residence time can be developed to more directly address both of these aspects of chromatography, but the existing surface delivery metrics already include some dispersion mitigation by requiring the exchange of high-speed core fluid with slow near-wall fluid.

Inlet/Outlet Designs

Figure 14:
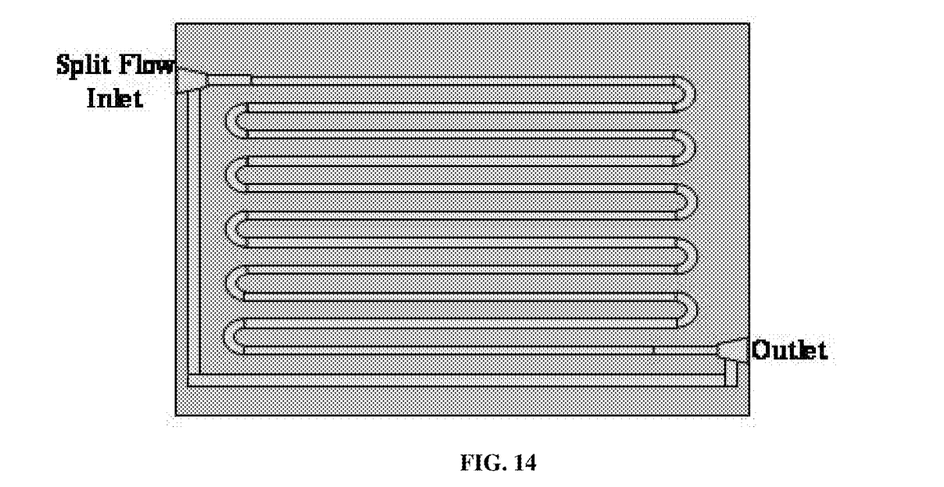
FIG. 14 shows a micro gas chromatograph design with a split flow injector.

High chromatographic resolution in a separation demands a small time width injection (e.g. <1 ms). In the present invention, this may be accomplished with a split flow injector—a T-junction is made at the inlet (could be valved for improved performance) with the wider part of the intersection being connected to the outlet while the regular GC column is more narrow and laid out in a serpentine fashion (FIG. 14). This also allows for continuous sampling to collect more of the analyte while minimizing pressure drop. The change in diameters results in a certain known ratio of the inflow being diverted to the micro gas chromatograph column every time without any valving mechanisms even though latching this system would definitely enhance the resolution. The wide inlet will also favor liquid sampling, but solid phase microextraction (SPME) cartridges can be inserted into the device.

A short segment with a thicker stationary phase coating at the inlet end of the column together with a dedicated heater may also be included in the present invention. This can serve as a focusing or preconcentrator device within the column itself, which can be flash-desorbed (with the dedicated heater in this zone) to provide a sharp analyte pulse injection into the micro gas chromatograph. This design eliminates any dead volume issues associated with a micro trap or preconcentrator device and allows very rapid injection times to offer improved chromatography performance. By selecting suitable sorbent materials for the preconcentrator, this can add improved selectivity to the analytical system. Microfabrication allows for the placement of three dimensional features like bumps or grooves on/in the walls of the inlet. This texturing of the inlet walls along with the use of sorbent polymer coatings may enhance the surface area for capture of analyte which will further increase the efficiency of the micro gas chromatograph system.

Chip designs that allow stacking for longer chromatographic path length with the same footprint can be facilitated by bringing the column inlet and outlet out of plane from the die and providing a simple stacking option. In this variation of the micro gas chromatograph design, the connections to the chromatographic column will be fabricated perpendicular to the actual die via deep reactive ion etching (DRIE). Again, alignment can be simplified by fabricating capillary connectors with exact measurements on opposite corners. The stacking will allow for multiple dies to be used in an analysis to gain additional length of the column and increased resolution. A variation might be to coat these stacked chips with the same or different polymers, for example polar and non-polar polymers. Furthermore, valving may be used in between these dies to apply GC "heart cuts" commonly used in conventional multi column systems.

Thermal Stability of Polymers in Air

In applications such as a micro gas analyzer, where portability is a requirement, utilizing air as the carrier gas eliminates the additional weight requirements of a nitrogen or helium gas tank. Unfortunately, traditional coatings in miniaturized gas chromatographs such as polysiloxanes, e.g. PDMS decompose in air at elevated temperatures (>159° C.). For the analysis of low vapor pressure analytes, elevated operating temperatures are required not only for the column but for all gas wettable surfaces prior to the detector to avoid loss of sample through condensation. In the present invention, functionalized carbosilane polymers may be utilized for the chromatographic stationary phase, for the analysis of organophosphates and a range of explosives at high temperatures (<280° C.). Using these custom sorbent polymers, e.g. HCSFA2, as a stationary phase in the micro gas chromatograph may provide thermal stability in air up to 280° C. for extended periods of time. Experiments show no significant change in HCSFA2 sorption properties over more than 1 year of use in air while being cyclically exposed to dimethyl methyl phosphonate and thermally cycled to 200° C. including several millions of thermal cycles.

Heating Schemes

Figure 15:
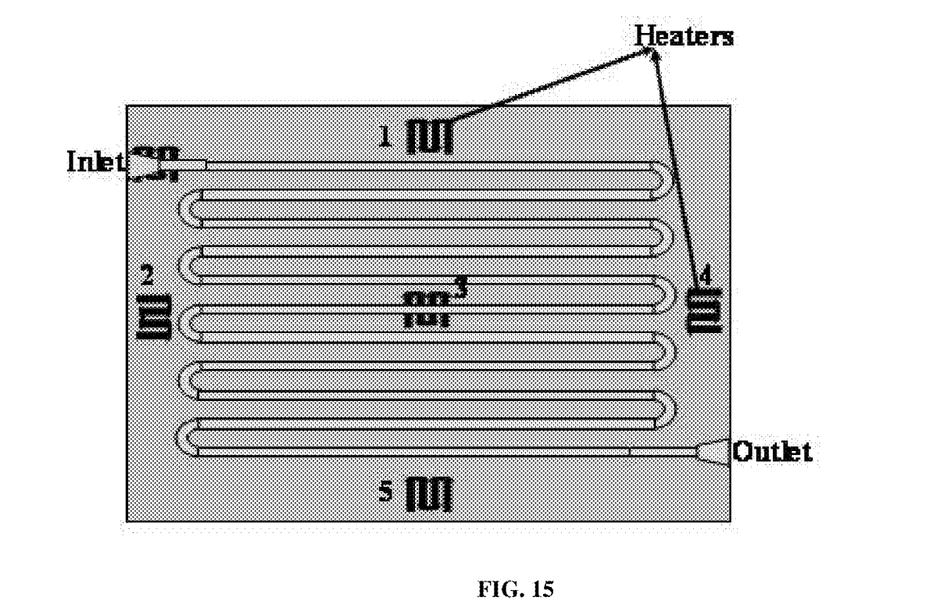
FIG. 15 is an illustration of a micro gas chromatograph die with integrated heaters.

Integrated on-chip heaters fabricated with doped polysilicon or metals such as Ti/Pt or Cr/Au allow for temperature programming (ramping as well as isotherms) in the micro gas chromatograph of the present invention. Raising column temperature during analysis increases the analyte vapor pressures resulting in shorter elution times, and allows rapid chromatographic separation of a wide range of analytes with different polarities and vapor pressures. Nominally, the heaters may be placed at the middle of each side and the center of the micro gas chromatograph die as shown in FIG. 15. As the die is about 1-2 cm square on each side, these five heaters can heat up the entire column. Another possibility is a separate heater for the inlet to allow for flash desorption and a sharp injection of a concentrated pulse into the column. The fact that they can be individually addressable through the wire bonds that connect to an externally controllable power supply means that the temperature of the column can be controlled accurately and sections of the columns can be heated sequentially. For example, the inlet heater could be heated up first to inject the analyte mixture followed by the other heaters in the order stated (1 through 5) thus shortening analysis times and saving electrical power. Furthermore, another option would be to heat all the resistors (1-5) at the same rate and time for isotherms which will result in a gain of about 25% peak capacity. Alternatively, the inside of the whole column (and/ or the outside if the column has been released) could be coated with a metal via sputtering or evaporation through a shadow mask to form a complete thin metal film that can provide more even heat distribution.

Pressure Programming

A concern for long narrow columns (e.g. 250 μm wide and 1-3 m long) is the pressure drop incurred. Pressure programming helps to maintain a constant flow in a column during analysis to avoid variation in retention times and thus degradation in separation efficiency. Researchers have shown that inlet dead volume costs more in terms of its contribution to band-broadening than outlet dead volume due to carrier gas compressibility. One way to reduce pressure drop or introduce sample effectively into the column in the form of a sharp pulse is to introduce head pressure—a chamber with a diaphragm at the inlet that can contract or expand thus changing volume and hence pressure. The actuation mechanism for the diaphragm may be electrostatic or via a magnetic force. Although this "pressure chamber" will not get rid of the pressure drop completely, with careful design and operation, the reduction may be sufficient for the analyte mixture to be successfully pushed through the column rather than pulled using a pump. Furthermore, it decreases the load on the pump and hence the power requirement.

The above descriptions are those of the preferred embodiments of the invention. Various modifications and variations are possible in light of the above teachings without departing from the spirit and broader aspects of the invention. It is therefore to be understood that the claimed invention may be practiced otherwise than as specifically described. Any references to claim elements in the singular, for example, using the articles "a," "an," "the," or "said," is not to be construed as limiting the element to the singular.

What is claimed as new and desired to be protected by Letters Patent of the United States is:

1. A microfabricated gas chromatograph column, comprising:
   a first substrate having a first pattern, said first pattern having a first stationary phase material coating selectively deposited on said first pattern;
   a second substrate having a second pattern wherein the second pattern is complementary to the first pattern, said second pattern having a second stationary phase material coating selectively deposited on said second pattern;
   a layer of adhesive between the first and second substrates bonding together the first and second substrates with the first and second patterns aligned to provide a continuous flow channel with at least one inlet and at least one outlet;
   a preconcentrator at the inlet comprising the first stationary phase material, the second stationary phase material, or both; and
   configured grooves in the first pattern, the second pattern, or both designed to improve fluid distribution in the flow channel.

2. The microfabricated gas chromatograph column of claim 1, wherein the first and second substrates each comprise silicon, glass, quartz, silicon nitride, silicon on insulator (SOI), or any combination thereof.

3. The microfabricated gas chromatograph column of claim 1, wherein the first pattern comprises a first series of consecutive turns in one direction followed by a second series of consecutive turns in the opposite direction and optionally followed by additional alternating series of consecutive turns, wherein each series comprises enough turns to move analyte molecules from the center of the column cross section to an outer wall of the channel or to move analyte molecules from an outer wall of the channel cross section to the center or the opposite outer wall of the channel.

4. The microfabricated gas chromatograph column of claim 1, wherein the adhesive is a low temperature adhesive that can be applied below a temperature that would decompose a stationary phase material.

5. The microfabricated gas chromatograph column of claim 4, wherein the adhesive is bis-benzocyclobutene.

6. The microfabricated gas chromatograph column of claim 1, wherein the first stationary phase material coating, the second stationary phase material coating, or both have a varying thickness of stationary phase material, a varying stationary phase material, or both.

7. The microfabricated gas chromatograph column of claim 1, wherein the first stationary phase material, the second stationary phase material, or both comprises carbon nanotubes.

8. The microfabricated gas chromatograph column of claim 1, wherein the first stationary phase material, the second stationary phase material, or both comprises a hydrogen bond acid sorbent polymer.

9. The microfabricated gas chromatograph column of claim 1, wherein the first substrate has a series of pins and the second substrate has a series of complementary tails to assist alignment.

10. The microfabricated gas chromatograph column of claim 1, wherein the channel has a substantially circular cross-section.

11. The microfabricated gas chromatograph column of claim 1, additionally comprising a heating element at the inlet.

12. A method of making a micro gas chromatograph, comprising the steps of:
    forming a first pattern onto a first substrate, said first pattern having a first stationary phase material coating selectively deposited on said first pattern;
    forming a second pattern onto a second substrate wherein the second pattern is complementary to the first pattern, said second pattern having a second stationary phase material coating selectively deposited on said second pattern;
    aligning the first and second patterns and bonding together the first and second substrates with an adhesive to provide a continuous flow channel with at least one inlet and at least one outlet;
    forming a preconcentrator at the inlet comprising the first stationary phase material, the second stationary phase material, or both; and
    configuring grooves in the first pattern, the second pattern, or both to improve fluid distribution in the flow channel.

13. The method of claim 12, wherein the first and second substrates each comprise silicon, glass, quartz, silicon nitride, silicon on insulator, or any combination thereof.

14. The method of claim 12, wherein the first pattern comprises a first series of consecutive turns in one direction followed by a second series of consecutive turns in the opposite direction and optionally followed by additional alternating series of consecutive turns, wherein each series comprises enough turns to move analyte molecules from the center of the column cross section to an outer wall of the channel or to move analyte molecules from an outer wall of the channel cross section to the center or the opposite outer wall of the channel.

15. The method of claim 12, wherein the adhesive is a low temperature adhesive that can be applied below a temperature that would decompose a stationary phase material.

16. The method of claim 15, wherein the adhesive is bis-benzocyclobutene.

17. The method of claim 12, wherein the first stationary phase material coating, the second stationary phase material coating, or both have a varying thickness of stationary phase material, a varying stationary phase material, or both.

18. The method of claim 12, wherein the first stationary phase material, the second stationary phase material, or both comprises carbon nanotubes.

19. The method of claim 12, wherein the first stationary phase material, the second stationary phase material, or both comprises a hydrogen bond acid sorbent polymer.

20. The method of claim 12, wherein the first substrate has a series of pins and the second substrate has a series of complementary tails to assist alignment.

21. The method of claim 12, wherein the channel has a substantially circular cross-section.

22. The method of claim 12, additionally comprising integrating a heating element at the inlet.

23. A microfabricated gas chromatograph column, comprising a channel having a first series of consecutive turns in one direction followed by a second series of consecutive turns in the opposite direction and optionally followed by additional alternating series of consecutive turns, wherein each series comprises enough turns to move analyte molecules from the center of the column cross section to an outer wall of the channel or to move analyte molecules from an outer wall of the channel cross section to the center or the opposite outer wall of the channel; additionally comprising configured grooves in the channel designed to improve fluid distribution.

* * * * *